(12) United States Patent
Davis et al.

(10) Patent No.: US 10,008,427 B2
(45) Date of Patent: Jun. 26, 2018

(54) SCANNING ACOUSTIC MICROSCOPE SENSOR ARRAY FOR CHIP-PACKAGING INTERACTION PACKAGE RELIABILITY MONITORING

(71) Applicant: International Business Machines Corporation, Armonk, NY (US)

(72) Inventors: Taryn J. Davis, Beacon, NY (US); Jonathan R. Fry, Fishkill, NY (US); Tuhin Sinha, Hackensack, NJ (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days. days.

(21) Appl. No.: 15/615,148

(22) Filed: Jun. 6, 2017

(65) Prior Publication Data

US 2017/0271219 A1 Sep. 21, 2017

Related U.S. Application Data

(62) Division of application No. 14/988,893, filed on Jan. 6, 2016.

(51) Int. Cl.

| | |
|---|---|
| *H01L 23/58* | (2006.01) |
| *H01L 21/66* | (2006.01) |
| *H01L 21/56* | (2006.01) |
| *H01L 21/48* | (2006.01) |
| *G01N 29/06* | (2006.01) |
| *H01L 23/498* | (2006.01) |

(52) U.S. Cl.
CPC ......... *H01L 22/26* (2013.01); *G01N 29/0681* (2013.01); *H01L 21/4853* (2013.01); *H01L 21/563* (2013.01); *H01L 22/12* (2013.01); *H01L 22/34* (2013.01); *H01L 23/49816* (2013.01); *H01L 23/49838* (2013.01); *H01L 2225/06596* (2013.01)

(58) Field of Classification Search
CPC ....... H01L 21/563; H01L 22/10; H01L 22/12; H01L 22/26; H01L 22/34; H01L 2225/06596; G01N 29/06; G01N 29/0681
USPC ............... 438/14–16; 257/48, 777, 778, 783
See application file for complete search history.

(56) References Cited

U.S. PATENT DOCUMENTS

| | | | | |
|---|---|---|---|---|
| 2009/0212377 A1* | 8/2009 | Vaganov | ............... | G06F 3/0338 257/415 |
| 2014/0355381 A1* | 12/2014 | Lal | ........................ | B81B 3/0021 367/87 |
| 2017/0008760 A1* | 1/2017 | Lloyd | ................... | B81B 7/0074 |

OTHER PUBLICATIONS

Davis, Taryn J. et al., "Scanning Acoustic Microscope Sensor Array for Chip-Packaging Interaction Package Reliability Monitoring"; U.S. Appl. No. 14/988,893, filed Jan. 6, 2016.

(Continued)

*Primary Examiner* — Matthew E Warren
(74) *Attorney, Agent, or Firm* — Cantor Colburn LLP; Steven Meyers

(57) ABSTRACT

A method includes forming a flip-chip module including a chip connected to a substrate with a layer of underfill material adhered to the chip and the substrate; sensing chip-packaging interaction failure in the underfilled flip-chip module in situ; reporting in-situ chip-packaging interaction failure to a device in real-time; and imaging the chip-packaging interaction failure with an indirect scanning acoustic microscope.

20 Claims, 8 Drawing Sheets

(56) References Cited

OTHER PUBLICATIONS

List of IBM Patents or Patent Applications Treated as Related; (Appendix P), Filed Jun. 8, 2017, 2 pages.

* cited by examiner

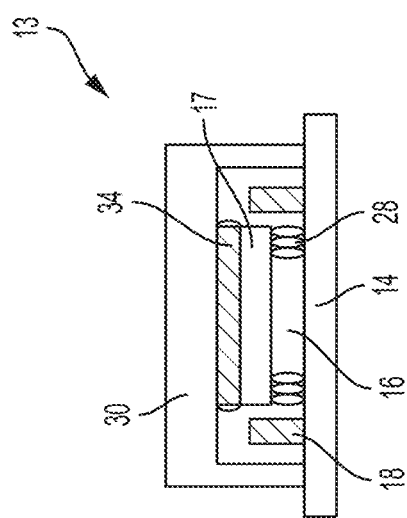
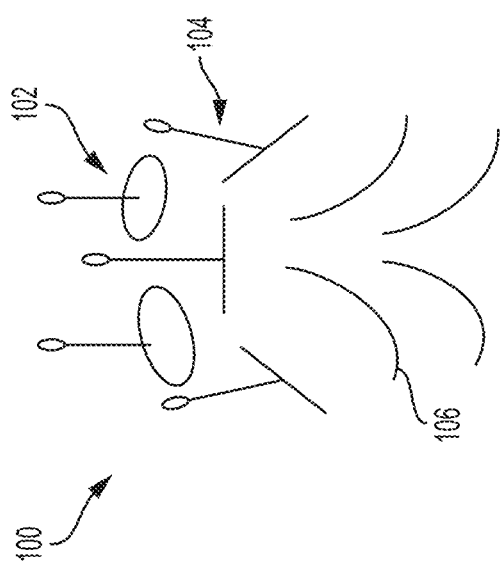

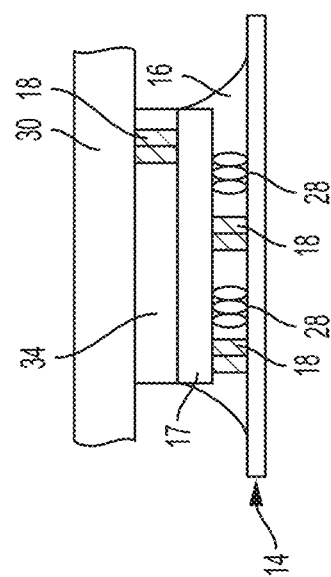
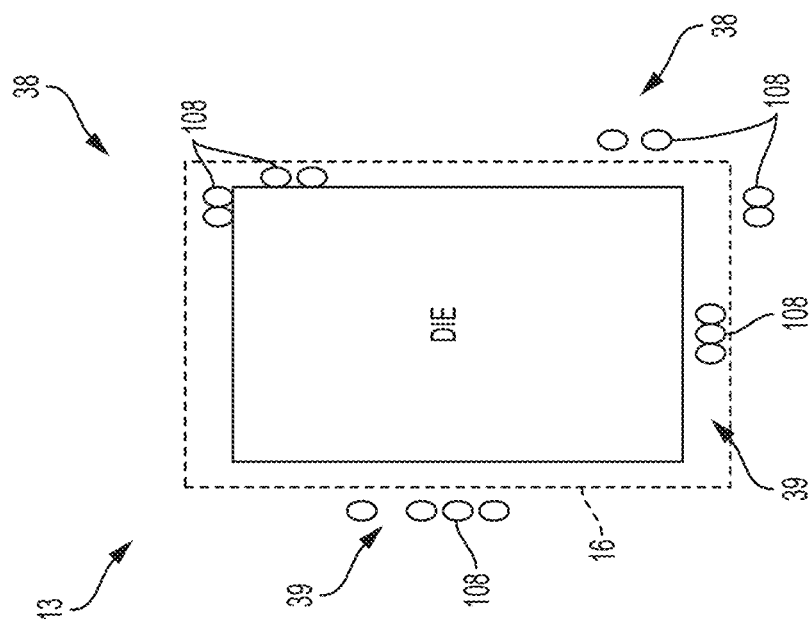

SCANNING ACOUSTIC MICROSCOPE SENSOR ARRAY FOR CHIP-PACKAGING INTERACTION PACKAGE RELIABILITY MONITORING

DOMESTIC PRIORITY

The present application is a divisional of U.S. patent application Ser. No. 14/988,893, filed on Jan. 6, 2016, which is hereby incorporated by reference in its entirety.

BACKGROUND

The present invention relates to a non-destructive method for detecting failure in a flip-chip module and a system therefore, and more specifically, to a non-destructive method for detecting delamination and crack propagation in a flip-chip module and a system.

Flip-chip technology includes methods for interconnecting semiconductor devices, such as integrated circuit (IC) chips to external circuitry using solder bumps that have been deposited onto chip pads. The solder bumps are deposited on the chip pads on a top side of a wafer to mount the chip to external circuitry (e.g., a circuit board or another chip or wafer). The wafer is flipped over so that its top side faces down, and aligned so that its pads align with matching pads on the external circuit, and then the solder is flowed to complete the interconnect. This technique is in contrast to wire bonding, in which the chip is mounted upright, and wires are used to interconnect the chip pads to external circuitry.

Flip chip assembly technology, wherein the integrated circuit chips are essentially flipped over and bonded to substrates using solderable interconnects, has seen rapid growth in semiconductor packaging in recent years. Alignment marks on the chip and the fiducial marks on the substrates are used for the fast automatic alignment between the chip and the substrate using a flip chip tool. The assembly of encapsulated flip chip circuit boards, however, remains a time consuming and expensive process. The key drivers for the demand for this technology are increased I/O connections enabling greater speed and shorter connections resulting in improved signal integrity.

In order for wafer level packaging to be successful, the flip chip tool must be able to align the integrated circuit chips (also referred to as a die) to the substrate. Normally, key features on the die and substrate are located using vision systems. These points are used as references in the alignment of the die and the substrate. Key features on the die are either fiducials or solder bumps. Key features on the substrate are either fiducials or bond pads. Two or more die may be stacked in a single package.

An integrated circuit substrate may comprise a number of layers. Some layers may comprise organic or ceramic dielectric material. Some layers may comprise conductors, such as traces, ground planes, and vias. An IC substrate may include an electronic component mounted on a surface of the substrate. The electronic component may be functionally connected to other elements of an electronic system through a hierarchy of conductors that include substrate traces, ground planes, and vias. The conductors may carry signals that are transmitted among the electronic components, such as integrated circuits, of the system. An integrated circuit substrate may have a relatively large number of input/output ("I/O") terminals (also called "lands"), as well as a large number of power and ground terminals or lands, on a surface of the integrated circuit substrate. An integrated circuit can include a lid which makes failure analysis like de-lidding and cross-sectioning irreversible/destructive.

The underfill material, which occupies the space between the flipped integrated circuit chip and the integrated circuit substrate, is important for reliability of the flip chip packages. Underfill material supports the electrical connections, protects them from the environment, and reduces the thermomechanical stress on the flip chip connection. The main reason for the thermal mechanical stress is the difference in coefficients of expansion (CTE) between the silicon chip and the organic laminate. For example the coefficient of thermal expansion of the silicon chip can be 1.0 to 15.0 parts per million per degrees Celsius (ppm/° C.) and the CTE for the organic laminate can be 12 to 25 ppm/° C. The CTE underfill material can be targeted to be close to the CTE of the solder interconnect which can be 22 ppm/° C. (low lead and lead free solders) to 28 ppm/° C. (high lead solders). The high modulus of elasticity (8 to 12 GigaPascals (GPa)) of the underfill material rigidly links the silicon and laminate over the entire area of the silicon and distributes the CTE mismatched thermal mechanical stress between silicon and laminate over the entire bonded area, rather than allowing the thermal mechanical stress to be concentrated at the solder joint, and cause fatigue fracture. In order to reduce this CTE mismatch, underfill materials typically contain inorganic filler, such as silica. Generally, the higher concentration of inorganic filler in the underfill material, the higher the thermal conductivity, which is desirable for high heat transfer so as to remove heat during operation of the chips.

It can be desirable to monitor the flip-chip module for failure causes by crack propagation or delamination of the underfill material before catastrophic failure without destroying the flip-chip module. Current methods include confocal mode scanning acoustic microscopy, electrical readout and probing of the controlled collapse chip connections, and destructive physical failure analysis by cross-sectioning the module. However, by the time the controlled collapse chip connection resistance has increased to the failure criteria, the damage in the module is so extensive that a root cause of the failure cannot be resolved. In fact, each of these methods fails to provide early failure detection or meaningful granularity for analysis or feedback. These methods are also time consuming, lab-intensive, expensive and/or destructive. These methods ultimately require more parts for stress qualification coming at a high cost with a large reliance on model assumptions.

SUMMARY

According to an embodiment, a method includes forming a flip-chip module including a chip connected to a substrate with a layer of underfill material adhered to the chip and the substrate; sensing chip-packaging interaction failure in the underfilled flip-chip module; reporting in-situ chip-packaging interaction failure to a device processor; and imaging the chip-packaging interaction failure with the device processor.

In another embodiment, a system comprises a flip-chip module package; a substrate connected to the flip-chip module; a layer of underfill material disposed between the flip-chip module and the substrate; and a sensor operative to measure acoustic impedance in the flip-chip module, wherein the sensor is embedded in the in a portion of the flip chip-module.

In another embodiment, a method includes forming a flip-chip module including a chip connected to a substrate with a layer of underfill material adhered to the chip and the substrate; sensing chip-packaging interaction failure in the underfilled flip-chip module in situ; reporting in-situ chip-packaging interaction failure to a device processor in real-time; and imaging the chip-packaging interaction failure with an indirect scanning acoustic microscope.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIG. 4A is a cross-sectional view of the components of a scanning acoustic microscopic set-up.

FIG. 4B is a cross-sectional view of the placement of scanning acoustic microscopy components in a flip-chip module.

FIG. 5 is a top view of a flip-chip module with various placements of scanning acoustic microscopy sensors.

FIG. 6 is a side view of a flip-chip module with various placements of scanning acoustic microscopy sensors.

DETAILED DESCRIPTION

Figure 1:
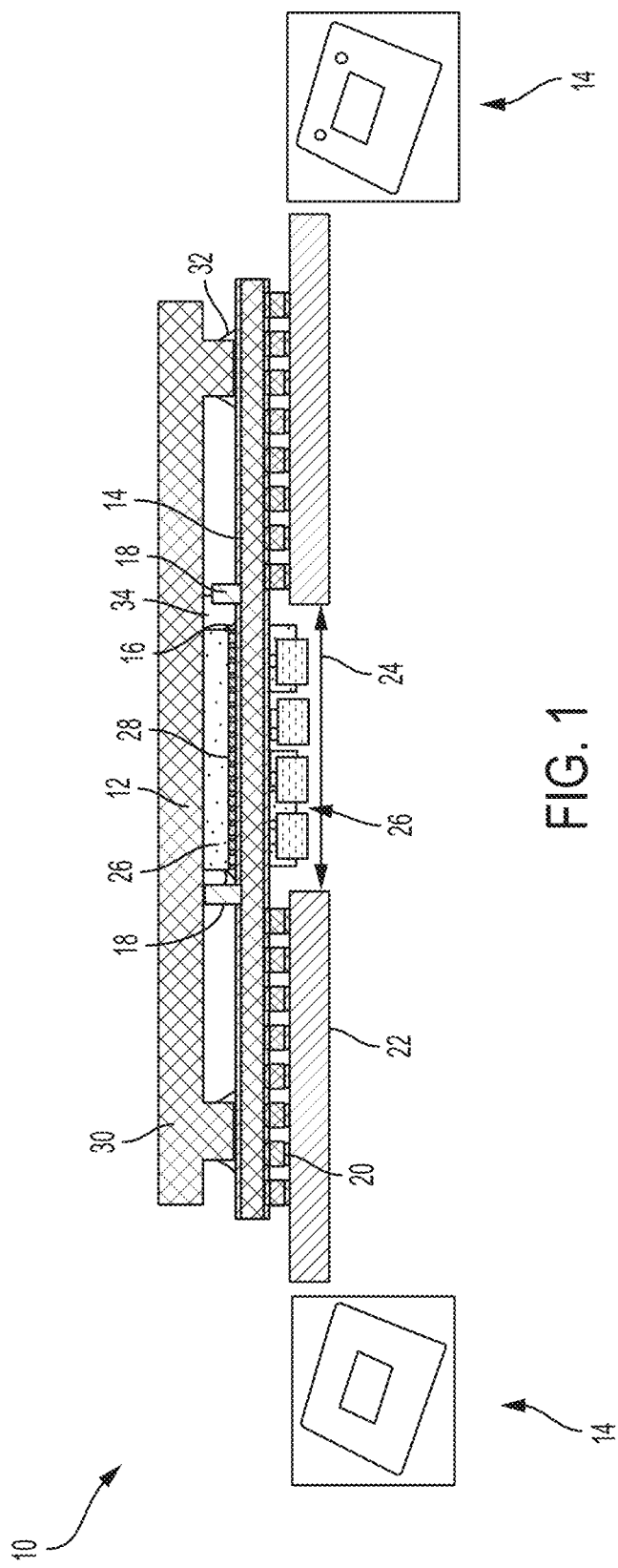
FIG. 1 is a cross-sectional illustration of a system for chip-packaging interaction reliability monitoring.

Disclosed herein are methods and systems for chip-packaging interaction (CPI) package reliability monitoring. The methods and systems can provide a non-destructive method for monitoring chip-packaging interaction failure before catastrophic failure of the flip-chip module. The methods and systems can include monitoring and reporting in-situ chip-packaging interaction failure to a device, e.g., a scanning acoustic microscope. The chip-packaging interaction failure can be imaged with the device. It can be possible to mitigate the chip-packaging interaction failure before catastrophic failure of the flip-chip module.

In the methods and systems disclosed herein individual or arrays of sensors or transducers can be places in and around various sections of an underfill material, e.g., in chip corners, for real-time tracking and diagnosis of crack propagation. The sensors/transducers can function as ultrasonic transceivers or ultrasonic transducers configured to provide higher resolution imaging in a scanning acoustic microscope device, or early warning, localized crack detection prior to catastrophic failure, such that first-cause/origin of failure mechanisms can be mitigated rather than second or third order failure mechanisms. This method can not only monitor early failures, but can also assist in understanding the rate, propagation and severity of cracking in real time.

The methods and systems disclosed herein can provide several advantages over prior methods by allowing early detection of non-critical, first cause failure, ahead of catastrophic electrical failure, by not performing destructive analysis of the flip-chip module thereby allowing study of crack propagation, by providing for in-situ continuous monitoring, and by advanced warning of field failures, allowing for service before users are impacted. Novel aspects of the presently disclosed system include an in-situ sensor approach, improve granularity spatially (e.g., location and type of fails) and temporally (e.g., propagation of fails, first cause), a non-destructive approach which enables continued stressing and fail propagation study.

This method and system provides the ability to detect non-critical "first fails" that can predict eventual catastrophic electrical failure, allowing for service with minimal customer impact or business interruption. The method and system provides a resolution in the location and rate at which the cracks propagate underneath the chip ultimately causing module failure. The method and system provides earlier detection than the current investigative methods meaning that the information can be collected more rapidly than current failure analysis processes, which can take several months to process a small number of parts. Because the system and method disclose herein provides timely analysis, every part can potentially be analyzed instead of the current few. Moreover, the system and method can provide a form of non-destructive analysis leading to the savings of thousands of dollars on building fewer test vehicles during reliability studies, and more information could be gained by having the ability to place the parts back on stress and watch how and where the failure develops.

As shown in FIG. 1, a system 10 as disclosed herein can include a flip-chip module 12, a substrate 14 connected to the flip-chip module 12, and a layer of underfill material 16 (also referred to herein as an underfill layer) disposed between the flip-chip module 12 and the substrate 14. The flip-chip module 12 can include a chip 26 and controlled collapse chip connections (C4) (e.g., solder balls) 28. A sensor 18 can be embedded in the layer of underfill material 16 in a portion of the flip-chip module 12. The system 10 can include a ball grid array 20. The ball grid array 20 can be disposed between the substrate 14 and a printed circuit board 22. The printed circuit board 22 can include a cutout portion 24 where capacitors 26 can be located. Capacitors 26 can be attached to the substrate 14 on an opposite surface as the underfill material 16. Optionally, a cover 30 can be attached to the flip-chip module 12 and the substrate 14. A sealing material 32 can be utilized to secure the cover 30 to the substrate 14. A heat dissipating material 34 (e.g., a thermal interface material) can be used between the flip-chip module 12 and the cover 30 to dissipate heat between the various components.

Figure 2:
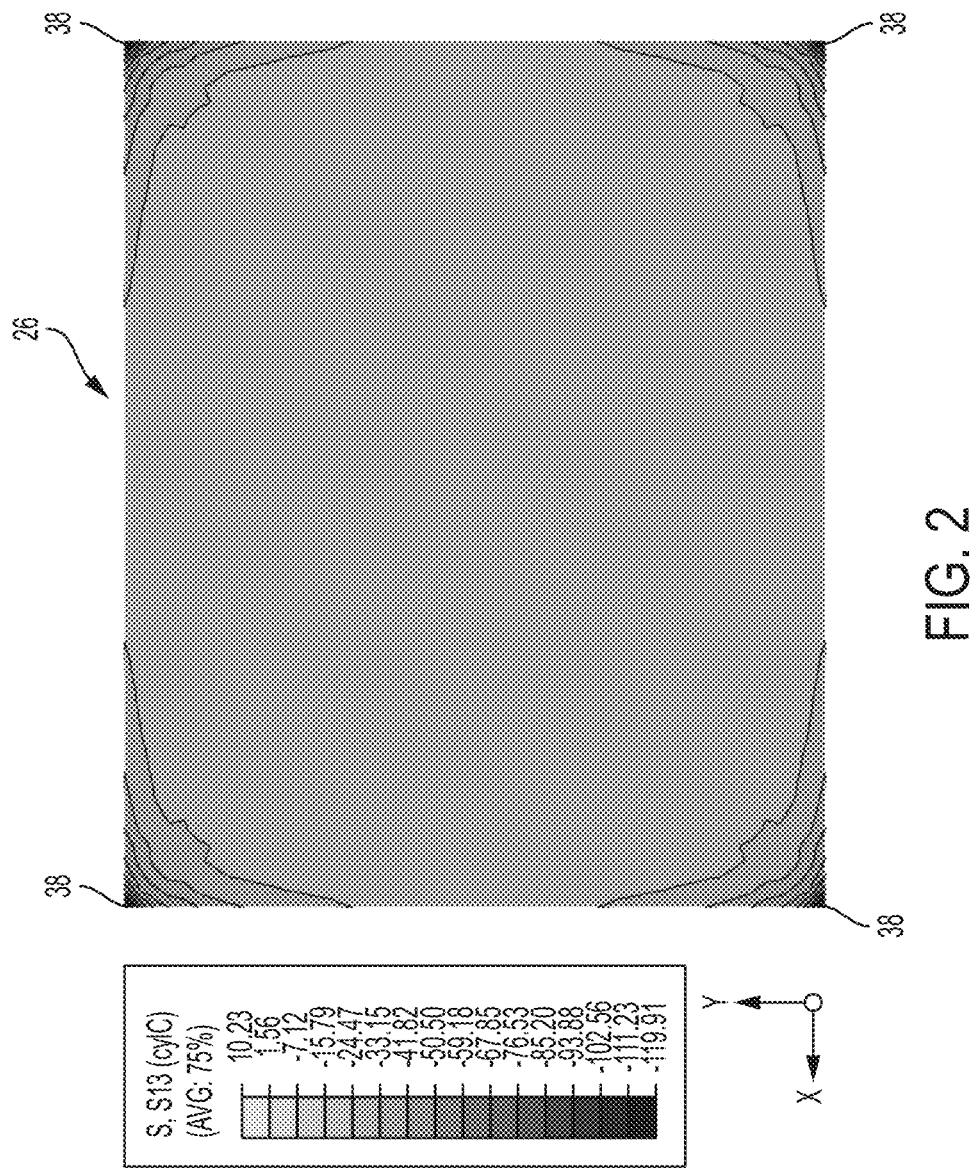
FIG. 2 is an illustration of the stress experienced by a flip-chip module.
Figure 3:
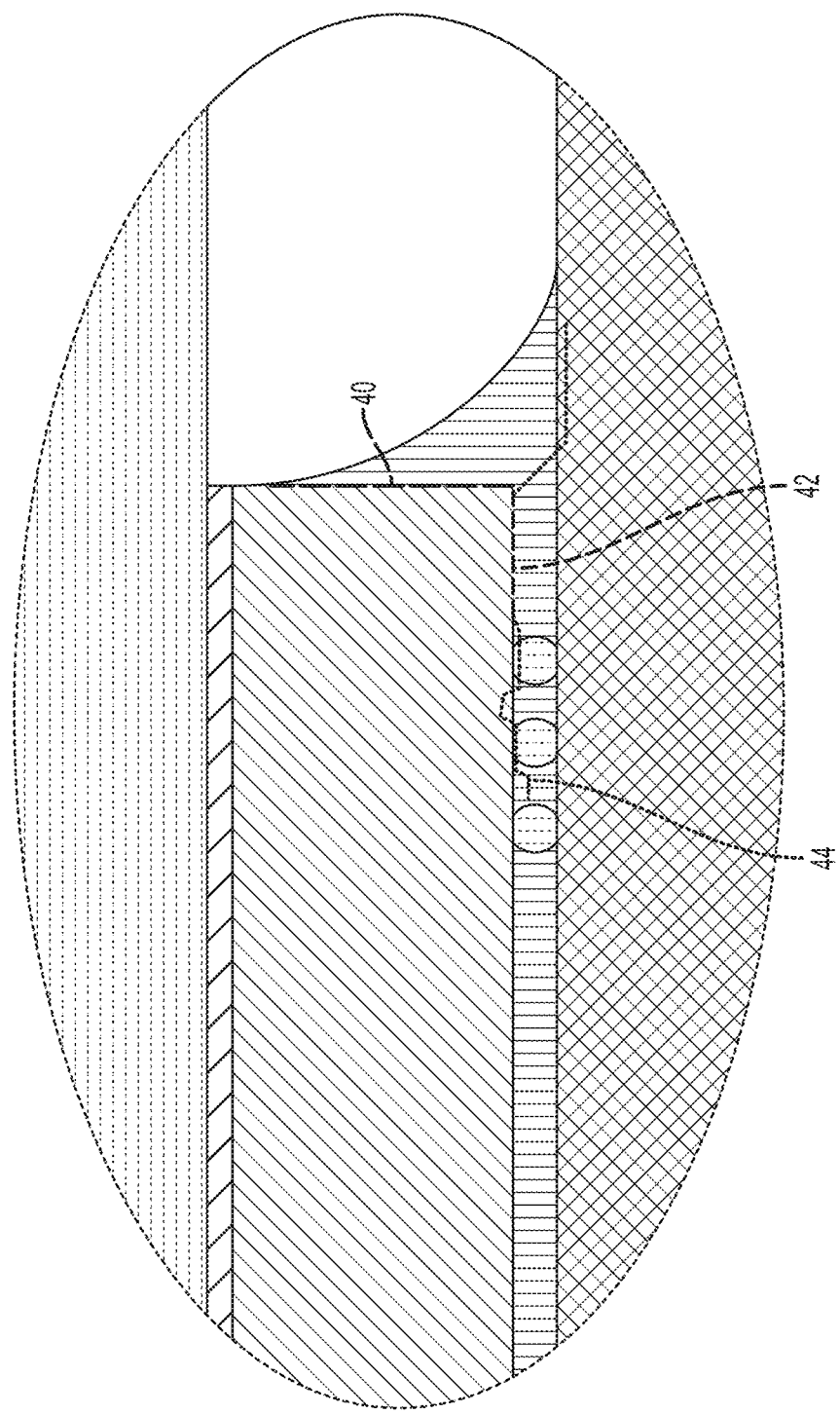
FIG. 3 is another illustration of the stress experienced by a flip-chip module.

A challenge in microelectronics flip-chip packaging is managing and/or mitigating the chip-packaging interaction stresses that occur in the flip-chip module due to a mismatch in the CTE between a silicon chip having a CTE of approximately 3 ppm/° C. and the organic laminate carrier (i.e., substrate). The CTE mismatch between the chip and the substrate creates increased mechanical stress that is highest in the chip corners 38 (e.g., corner regions) as illustrated in FIG. 2. The increased mechanical stress at the chip corners 38 can result in crack propagation in regions including, but not limited to, underfill sidewall delamination 40, bulk underfill cracking 42, and underfill to chip delamination 44 underneath the chip as shown in FIG. 3.

Underfill sidewall delamination and bulk underfill cracking can damage the mechanical integrity of the flip-chip module, but do not directly affect the electrical performance of the flip-chip module. Crack propagation under the chip can ultimately terminate in the chip or controlled collapse chip connections (C4) (e.g., solder balls), thereby severing the electrical pathway and causing failure of the flip-chip module.

The system disclosed herein can include a heat sink package that is air or liquid cooled. As described, a sensor 18 (e.g., an acoustic transducer/transceiver) can be placed along or under edges of the chip 26. The sensor 18 can be embedded in the substrate 14. The underfill layer 16 can function as a signal transmission medium compared to water in a confocal scanning acoustic microscopy. A strong difference in signal transmission exists between the air/cracks and the underfill layer 16. Frequency boosters, frequency shifters, frequency directional arrays can also be used.

Tx (Transmit) components and Rx (Receive) components are separate design elements in most design libraries (micro-electro-mechanical systems (MEMS) or otherwise). In the present application, acoustic transmit-receive hardware, and not the methodology of offloading signals and data from the sensor is considered. The system can be constructed in a number of ways using one or both components, in conjunction with external SAM (Scanning Acoustic Microscopy) equipment.

The sensors do not directly generate imagery; rather, they gather acoustic signals. The process of creation of imagery from knowing the geometry of the Tx and Rx components of an array, coupled with signal processing techniques can recreate an image (for example, the techniques that drive SAM and MRI imagery use related image-reconstruction-from-spectra techniques). However changes in the state of the system can be directly noted by changes in spectra without necessarily reconstructing an image. This could be done by a small microprocessor. Using multiple pings from multiple Tx devices and multiple samples from multiple Rx devices can be used to create more detailed images.

In a Use Case 1 with the Tx Mode in SAM, the acoustic source (Tx) of the SAM microscope can be used to disable the microphone (Rx) of the SAM. The acoustic pings propagate through the medium in the SAM chamber (e.g., water). Some of the acoustic energy is reflected off of the lid of the package (backscatter) and is re-absorbed by the chamber. It is for this reason that lidded modules cannot be imaged in SAM; the amplification of the backscatter signal is orders of magnitude stronger than any subtle resonance signals originating from the package, and signal processing cannot overcome this fundamental signal-to-noise ratio problem. Some of the acoustic energy propagates through the package and vibrates/excites the structures in the package and produces a new resonance spectrum. The resonance spectra is captured by the sensor(s) in and around the die, digitized and exported for image reconstruction and analysis.

In a Use Case 2 with the Rx Mode in SAM, the microphones (Rx) of the SAM are utilized and the acoustic source of (Tx) of the SAM is disabled. The acoustic pings are created by the Tx hardware in the sensor unit. The pings propagate through the package and create new resonance spectra. Some of the energy is lost in transmission through the lid. The remainder of the energy reaches the SAM microphones and can be amplified through a high-gain stage (no backscatter to interfere) to reconstruct the signal. The resonance spectra is captured by the SAM microphones, digitized and exported for image reconstruction and analysis.

In a Use Case 3 with the Tx/Rx Mode in Sensor Only (i.e., in situ, no SAM), the acoustic source (Tx) of the sensor is used to create a ping. The pings propagate through the package and create new resonance spectra. The receiver (Rx) of the sensor captures the resonance spectra, is digitized, and exported for image reconstruction and analysis.

FIG. 4A shows a schematic of the SAM signal 100 where a SAM microphone 102 has a SAM acoustic source 104 and an acoustic ping 106. FIG. 4B shows a flip-chip module 13 with sensors 18 disposed therein. For example, FIG. 4B shows a substrate 14 connected to a dielectric layer 17 with a layer of underfill material 16 (also referred to herein as an underfill layer) disposed therebetween. The flip-chip module 13 can include controlled collapse chip connections (C4) (e.g., solder balls) 28. A sensor 18 can be embedded in the layer of underfill material 16 in a portion of the flip-chip module 12. Optionally, a cover 30 can be attached to the flip-chip module 13 and the substrate 14. A heat dissipating material 34 (e.g., a thermal interface material) can be used between the flip-chip module 13 and the cover 30 to dissipate heat between the various components.

FIG. 5 and FIG. 6 illustrate sensor placement examples. In FIG. 5, which is a top down view of a flip-chip module 13 (with no cover shown), Tx and Rx sensors 108 are distributed in the underfill material 16 at corner regions 38 and outside the underfill material 16 at a center edge 39. The same is shown in FIG. 6, which is a side view of the flip-chip module 13 shown in FIG. 5.

Figure 7:
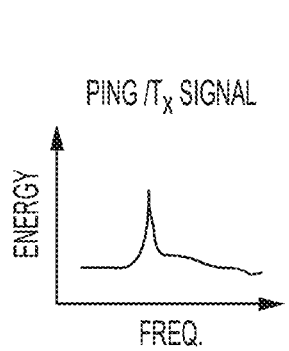
FIG. 7 is a graphical illustration of the transmission signal at an acoustic ping.
Figure 8A:
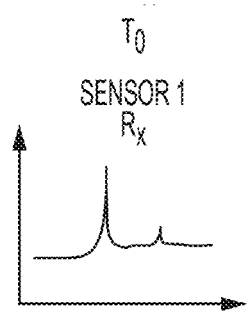
FIGS. 8A to 8D are graphical illustrations of receiver sensors at a time, $T_0$.
Figure 9A:
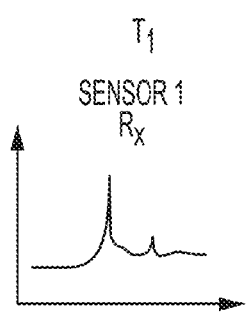
FIGS. 9A to 9D are graphical illustrations of receiver sensors at a time, $T_1$.
Figure 8B:
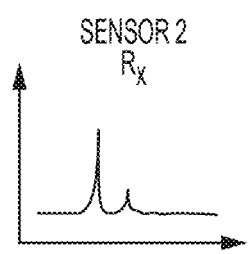
Figure 9B:
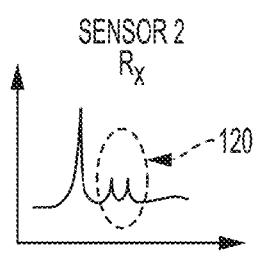
Figure 8C:
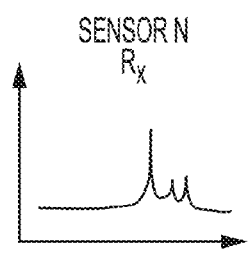
Figure 9C:
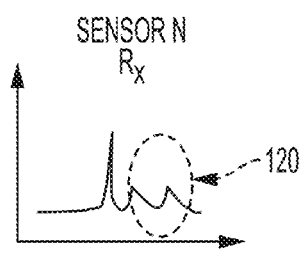
Figure 8D:
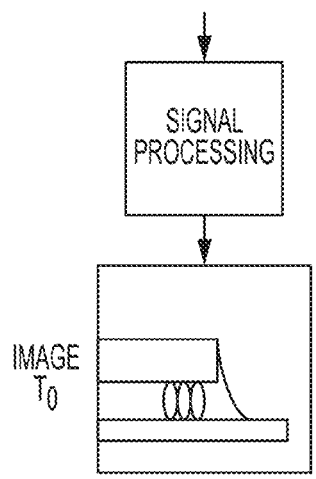
Figure 9D:
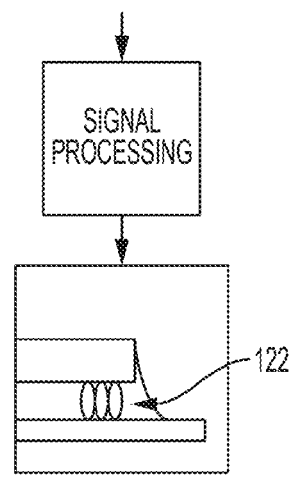

FIG. 7 is a graphical illustration of the energy versus frequency of a Tx signal ping where a peak is observed at the ping. FIGS. 8A to 8D illustrate Rx signals at $T_0$ and FIGS. 9A to 9D illustrate Rx signals at $T_1$. There is a shift 120 in the spectra from T0 to T1 from FIG. 8B to FIG. 9B and from FIG. 8B to FIG. 9B with Sensor 2 and Sensor N, respectively. Signal processing can provide images in FIG. 8D and FIG. 9D with a crack 122 appearing in FIG. 9D.

The method disclosed herein can monitor and report the failure without destroying the flip-chip module. For example, the sensor 18 can include an acoustic transducer/transceiver that can provide an acoustic response to a scanning electronic microscope collector. The acoustic response can be translated into an image demonstrating where and how the failure is occurring. The method includes the advantage of a lack of backscattering which allows for the image to be refined without destruction. The transducer/transceiver can decode the acoustic response to localize where the fault is occurring.

In an exemplary embodiment, the method disclosed herein can include (1) at time (T) equal to ° Baseline, an undamaged package has a specific acoustic impedance signature (X), which can be extracted by real-time monitoring of a sensor array; (2) at T=M/first crack, a crack occurs, allowing air into the underfill layer or other region with known acoustic impedance signature. This causes the acoustic impedance signature to shift from (X) to (Y). The usage of multiple sensors spatially localizes the fault. It is be noted that this detection occurs before any electrical or functional failure; (3) at T=N/secondary effects), continued monitoring of the acoustic impedance signatures and spatial localization tracks the worsening of the initial crack and secondary cracking and effects; (4) T=P/first hard catastrophic fail, first electrical or mechanical failure of the package can be correlated back to impedance signatures. The difference between M and P can establish the opportunity for field service given early detection at time M. Since hard failure is not necessarily caused by the 2nd and 3rd order effects (i.e., Time N), there can be a more reliable understanding of the life span of the device. The progression of M-N-P can also describe the propagation of cracks in real time, and can benchmark solutions such as crack stops among other failure mitigating solutions.

A method of mitigating chip-packaging interaction failure before catastrophic failure of the flip-chip module can include forming a flip-chip module including a chip connected to a substrate with a layer of underfill material adhered to the chip and to the substrate, sensing chip-packaging interaction failure in the underfilled flip-chip module; reporting in-situ chip-packaging failure to a device processor 114 with an input device 112, and imaging the chip-packaging interaction failure with the device processor 114. The image can be saved in a memory 118. Data associated with the image can be outputted to a user on a display 116.

Figure 10:
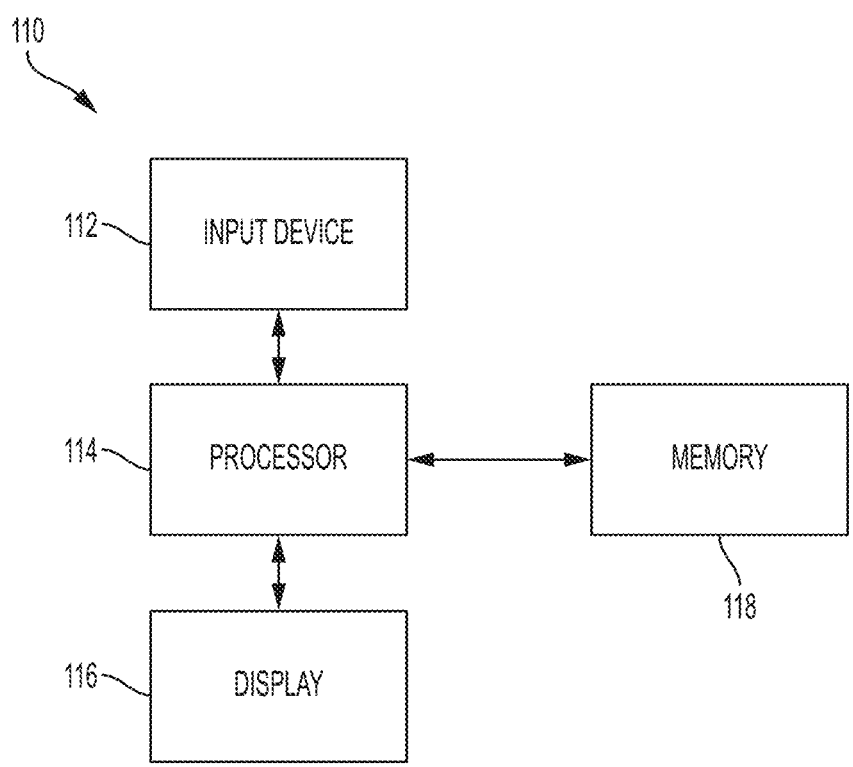
FIG. 10 is a block diagram of an exemplary embodiment of a system for chip-packaging interaction reliability monitoring.

FIG. 10 shows a block diagram of an exemplary embodiment of a processing system 110. The system 110 includes a processor 114 that is communicatively connected to a memory 118, a display 116, and an input device 112. In this regard, portions of the methods and systems described herein can be performed on the system 110.

Figure 11:
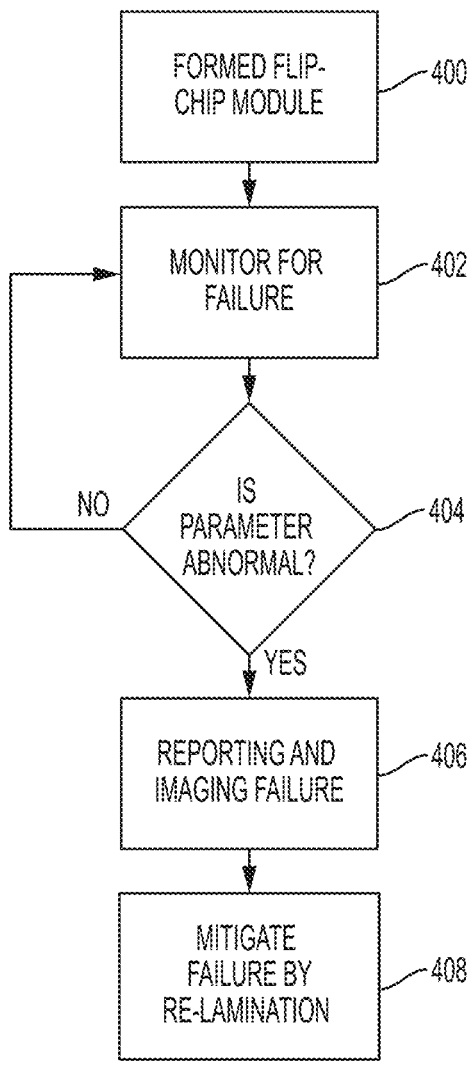
FIG. 11 is a flow diagram of an exemplary embodiment of the operation of the system of FIG. 10.

FIG. 11 shows a flow diagram of an exemplary embodiment of the operation of the system of FIG. 10. Referring to FIG. 11, in block 400, a flip-chip module has been formed. In block 402, the flip-chip module is monitored for chip-packaging interaction failure (e.g., delamination). In block 404, if the parameters are abnormal (e.g., the acoustic pings are above or below a threshold number that indicated delamination), the failure is reported to the device processor 114 and an image formed as shown in block 406. After reviewing the image for failure, the damage can be mitigated by re-lamination of the underfill material as seen in block 408.

In a small sensor array approach, each sensor is a fully active acoustic transceiver with a detection region focused in a specific spatial location, either using independent sensing techniques, or constructive-interfering array techniques to resolve cracks.

In a local power remote detect approach, by placing the acoustic resonators at or near the source of the area of interest, the gain of the power array of the confocal scanning acoustic microscope can be deactivated. As a result, the gain stage of the confocal scanning acoustic microscope can be greatly enhanced. This can assist in solving a drawback of using scanning acoustic microscopy which is that the sensor array is also essentially the energizing array, and resolving images becomes a hefty signal-to-noise reconstruction problem.

Both the small sensor array approach and the local power remote detect approach can be powered directly electrically (i.e., wired), or through radio frequency energizing. Acoustic energy can be generated in mems structures (such as surface acoustic wave sensors or even basic piezoelectric structures. The frequency of these devices can be tuned based on application specifics of the chosen packaging materials for the underfill layer, the substrate, etc.

Delamination manifests as white spots due to the relative difference of the acoustic impedance of air (i.e., the crack) and other materials.

In another embodiment, the process includes photolithography to precisely impart low surface tension surface to the alignment marks. In this process, a photoresist is deposited onto the wafer and exposed through a mask, wherein the mask includes openings corresponding to the alignment openings as in the case of a positive acting photoresist or covers the alignment marks in the case of a negative acting photoresist such that development of the photoresist after exposure exposes the alignment marks.

A self-assembling low surface tension material can then be applied via spin coating, spraying, immersion, or the like onto the wafer. By way of example, a low surface tension material such as a solution of octadecyltrichlorosilane in toluene or a solution of polytetrafluoroethylene in a perfluorinated solvent can be applied. The wafer is then heated to form a stable coating, e.g., the polytetrafluoroethylene solution can be heated to about 310° C. to about 330° C. for a period of about 10 to 15 minutes to fix the coating.

It should be noted that in some embodiments, the extreme corners of the die may not need the self-assembling low surface tension material since these areas generally need underfill protection (by structural coupling) more than other areas. In this manner, only a portion of the alignment marks are needed to provide alignment and effective bonding of the flip-chip to the substrate. As such, the alignment marks can be in the center of the die, in the center and off center, or any other areas, which in some embodiments may include the corners. For alignment marks having dimensions less than about 1 micrometer, the use of photolithography to expose the alignment marks for subsequent coating with the low surface tension material may be preferred.

The layer of underfill material can then be deposited. For example, the underfill material deposited on the wafer can be "b-staged." In the art, a b-stage resin is a thermosetting resin reacted to a stage where it is hard at room temperature and essentially solvent free but still flows when heated above its b-stage glass transition temperature (Tg). It is a preferred stage for a resin when it is being molded. In the step where the wafer is b-staged, the solvent is removed and the crosslink reaction is advanced to significantly below the gel point with the goal to render the b-staged underfill surface generally tack free and to impart desired b-stage Tg and flow properties. After depositing the underfill materials, die cutting occurs. The underfill materials are not intended to be limited to any particular type and are generally polymer based materials that can contain inorganic filler(s) to approximate the CTE of the solder joint as described above.

In an embodiment, the underfill material can comprise a thermally reversible material. "Thermally reversible", as used herein, means that the material may be repeatedly heated and cooled without substantially altering the inherent physical or chemical properties of the material, except that it becomes relatively less viscous as it is heated, and it becomes relatively more viscous as it is cooled.

Using a thermally reversible material in underfill can enable the electronic assembly to be reworked, by heating underfill material suitably for it to become less viscous again. The ability to rework electronic assemblies, such as electronic assembly, is an advantage, because it may decrease manufacturing costs.

A thermally reversible network polymer can contain thermally reversible covalent crosslinks. At room temperature, the material is relatively solid and may have adhesion, CTE (coefficient of thermal expansion), dielectric, mechanical, and other properties similar to an epoxy thermoset underfill. At higher temperature, these crosslinks dissociate to yield a low-viscosity substance, and when it is subsequently cooled the substance readily polymerizes to regenerate the original solid network polymer.

Although, in an embodiment, a thermally reversible network polymer is used, in other embodiments a non-thermally reversible polymeric adhesive can be used, for example, if reworkability is not desired.

As an alternative to a polymeric adhesive, the underfill material can comprise a thermoset plastic, an unlinkable epoxy, or other materials having properties similar to or identical to those described herein. Epoxy resins can be desired for a number of diverse applications including coatings, adhesives, structural materials, electrical insulation, encapsulants, etc. Epoxy formulations have outstanding properties after curing, including, but not limited to, toughness, adhesion and solvent resistance.

The flow characteristics of underfill material can be selected such that underfill material is not sticky (or relatively unsticky) at room temperature. Thus it can be used with known IC manufacturing equipment, such as pick-and-place equipment.

Inorganic filler can be used to lower the overall coefficient of thermal expansion (CTE) of the polymer layer, and accordingly, of the layer of underfill material. The inorganic filler used in herein can be non-conductive, and inert, meaning that it will not react with or destabilize the polymer layer. An amount of inorganic filler is used in the polymer layer in order to get the CTE of the underfill close to the relatively lower CTE of the solder balls. The proper choice of CTE can be desirable for stress mitigation during manufacturing and subsequent use of the electronic assembly.

Fillers used in the formulation for the layer of underfill material can be present in an amount of 5% to 75% by weight, for example, 30% to 65% by weight, and can be any of the powdered solids including alumina, silica, zinc oxide, boron nitride, talc, titanium oxide, zirconia, berylia, ceria, silicon nitride, aluminum nitride, silicon carbide, Al, Ag, Cu, TiO2, clay, or a combination comprising at least one of the foregoing. Mixtures of inorganic filler can be used. The inorganic filler can have any desired shape and size. The inorganic filler can have a spherical or substantially spherical shape. Such spherical shape can minimize surface area and can allow for a higher loading of filler in the polymer region. It can be desirable that the inorganic filler has a size, such as a particle size, that will not impede the penetration of the second polymer region by interconnect structures. It can be desirable that the inorganic filler has a mean particle size of 0.005 to 10 micrometers ($\mu$m), for example, 0.01 to 5 $\mu$m, and for example, 0.01 to 3 $\mu$m. The inorganic filler can be optionally be treated with an adhesion promoter to modify the surface chemistry of the filler particle, for example, to allow the inorganic filler particle to react with the polymer or crosslinker used in the polymer region. Modifying the surface chemistry of the filler can improve fracture toughness and can improve the dispersion of the filler in the polymer region. All ranges disclosed herein are inclusive of the endpoints, and the endpoints are combinable with each other.

The substrate can include an organic material, a ceramic material, or a combination comprising at least one of the foregoing. For example, the substrate can include a glass ceramic, glass, an organic material comprising a composite including a curable resin as a dielectric and glass-cloth as the core. Copper traces and filled copper can be included in the substrate.

The thermal interface material can include silicone gels filled with alumina, boron nitride, graphite particles, or a combination comprising at least one of the foregoing.

The sealing material can include an epoxy as described herein with respect to the layer of underfill material.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a flip-chip module package;
a substrate connected to the flip-chip module;
a layer of underfill material disposed between the flip-chip module and the substrate; and
a sensor operative to measure acoustic impedance in the flip-chip module, wherein the sensor is embedded in the in a portion of the flip chip-module
wherein the underfill material comprises an inorganic filler;
wherein the inorganic filler is present in an amount of 5 to 75% by weight of the layer of underfill material.

2. The system of claim 1, wherein the sensor feeds data to a scanning system.

3. The system of claim 2, wherein the scanning system includes a scanning acoustic microscope.

4. The system of claim 1, wherein the sensor includes an array of sensors disposed in a corner region of the flip-chip module.

5. The system of claim 4, wherein the array of sensors are disposed in at least two corner regions of the flip-chip module.

6. The system of claim 1, wherein the sensor includes an array of sensors disposed in a portion of the underfill material, outside the underfill material, or a combination comprising at least one of the foregoing.

7. The system of claim 1, wherein the substrate comprises glass, an organic material, a ceramic material, or a combination comprising at least one of the foregoing.

8. The system of claim 7, wherein the substrate comprises an organic material comprising a composite including a curable resin and a glass-cloth.

9. The system of claim 1, wherein the underfill material comprises a thermally reversible material.

10. The system of claim 9, wherein the underfill material is thermoplastic material, a thermoset material, an epoxy material, or a combination comprising at least one of the foregoing.

11. The system of claim 1, wherein the inorganic filler is non-conductive and/or inert.

12. The system of claim 1, wherein the underfill is present in an amount of 30 to 65% by weight.

13. The system of claim 1, wherein the underfill material comprises alumina, silica, zinc oxide, boron nitride, talc, titanium oxide, zirconia, berylia, ceria, silicon nitride, aluminum nitride, silicon carbide, Al, Ag, Cu, TiO2, clay, or a combination comprising at least one of the foregoing.

14. The system of claim 1, wherein the inorganic filler has a mean particle size of 0.005 to 10 micrometers.

15. The system of claim 1, wherein the flip-chip module further includes a ball grid array.

16. The system of claim 1, wherein the flip-chip module further includes a cover disposed over the flip-chip module, opposite the substrate.

17. The system of claim 1, wherein the data provided includes spatial data and temporal data.

18. The system of claim 17, wherein the spatial data includes location and type of fails and wherein the temporal data includes propagation of fails and first cause.

19. The system of claim 1, wherein the inorganic filler has a modified surface chemistry.

20. The system of claim 19, wherein the inorganic filler has improved dispersion in the underfill material as compared to an inorganic filler without a modified surface chemistry.

* * * * *